(12) United States Patent
Bogdanovic et al.

(10) Patent No.: US 6,191,063 B1
(45) Date of Patent: Feb. 20, 2001

(54) CATALYST AND PROCESS FOR THE PRODUCTION OF ALDEHYDES BY HYDROFORMYLATION OF OLEFINICALLY UNSATURATED COMPOUNDS

(75) Inventors: Sandra Bogdanovic, Frankfurt; Carl-Dieter Frohning, Wesel; Helmut Bahrmann, Hamminkeln; Matthias Beller, Rostock; Steffen Haber, Königstein; Hans-Jerg Kleiner, Kronberg, all of (DE)

(73) Assignee: Celanese GmbH, Oberhausen (DE)

( * ) Notice: Under 35 U.S.C. 154(b), the term of this patent shall be extended for 0 days.

(21) Appl. No.: 09/230,576
(22) PCT Filed: Jul. 21, 1997
(86) PCT No.: PCT/EP97/03926
  § 371 Date: Jul. 1, 1999
  § 102(e) Date: Jul. 1, 1999
(87) PCT Pub. No.: WO98/04346
  PCT Pub. Date: Feb. 5, 1998

(30) Foreign Application Priority Data

Jul. 29, 1996 (DE) .............. 196 30 536
Apr. 30, 1997 (DE) .............. 197 18 195

(51) Int. Cl.[7] .............. B01J 31/28; C07C 45/50
(52) U.S. Cl. .............. 502/166; 502/213; 556/21; 556/136; 568/451; 568/454
(58) Field of Search .............. 556/136, 21; 568/451, 568/454; 502/166, 213

(56) References Cited

PUBLICATIONS

Chemical Abstracts, vol. 25, No. 3, 1996, p. 855, #XP002043597.
Chemical Abstracts, vol. 105, 1986, p. 622, #XP002043598.
Patent Abstracts of Japan, vol. 096, No. 002, Feb. 29, 1996 and JP 07 267890 A (Kurraray Co., Ltd.), Oct. 17, 1995.
Polymer Communications, vol. 36, No. 15, 1995, pp. 3035–3039.

*Primary Examiner*—Sreeni Padmanabhan
(74) *Attorney, Agent, or Firm*—Frommer Lawrence & Haug LLP

(57) ABSTRACT

A catalyst comprising rhodium and a compound of the formula (I)

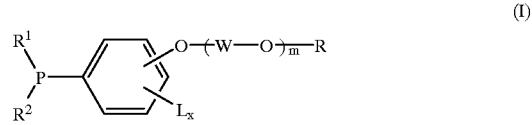

in which
m is a number from 1 to 1000;
x is a number from 0 to 4;
W is a group of the formulae $-CH_2-CH_2-$, $-CH(CH_3)CH_2-$ or $-CH_2CH(CH_3)-$;
R is hydrogen, a straight-chain or branched $C_1-C_5$-alkyl radical; or a group of the formulae

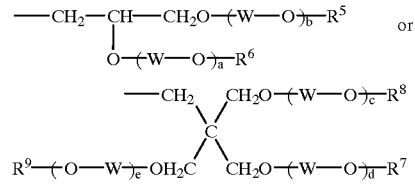

where
a, b, c, d and e independently of one another are a number from 0 to 1000, at least one of the numbers a, b, c, d and e being greater than 0;
$R^5$, $R^6$, $R^7$, $R^8$ and $R^9$ are identical or different and are hydrogen, $C_1-C_5$-alkyl or a group of the formula

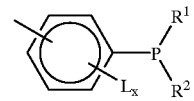

$R^1$ and $R^2$ are identical or different and are a straight-chain, branched or cyclic $C_1-C_{30}$-alkyl radical or $C_{6-10}$-aryl radical, which is unsubstituted or substituted by from one to five $C_1-C_3$-alkyl radicals, and
L is $C_1-C_5$-alkyl, $C_1-C_5$-alkoxy, $NO_2$, $NR^3R^4$, where $R^3$ and $R^4$ independently of one another are hydrogen or $C_1-C_4$-alkyl, or L is Cl or OH,
for hydroformylation reactions.

14 Claims, No Drawings

CATALYST AND PROCESS FOR THE PRODUCTION OF ALDEHYDES BY HYDROFORMYLATION OF OLEFINICALLY UNSATURATED COMPOUNDS

This is the U.S. National Stage Application of PCT/EP97/03926 filed Jul. 21, 1997.

The invention relates to a novel catalyst and to a process for the hydroformylation of olefinically unsaturated compounds, whose hydroformylation products are insoluble or virtually insoluble in water, in the presence of this catalyst.

It is known that by reacting olefins with carbon monoxide and hydrogen (hydroformylation), it is possible to prepare aldehydes and alcohols which contain one more carbon atom than the starting olefin. The reaction is catalyzed by hydridometal carbonyls, preferably those of the metals of group VIII of the Periodic Table. Besides cobalt, the classic catalyst metal, catalysts based on rhodium have been increasingly used for some years. In contrast to cobalt, rhodium allows the reaction to be carried out at low pressure, and moreover when terminal olefins are used, straight-chain n-aldehydes are formed preferentially and isoaldehydes are formed only to a subordinate degree. Finally, the hydrogenation of olefinic compounds to give saturated hydrocarbons in the presence of rhodium catalysts is also significantly lower than when cobalt catalysts are used.

In industry, the hydroformylation of olefinically unsaturated compounds using the catalytic effect of rhodium-phosphine complex compounds is essentially carried out in two variants. The first involves the process being carried out in homogeneous phase, i.e. starting olefin, catalyst system (rhodium carbonyl and organic phosphine) and reaction products are present in solution together. The reaction products are separated off from the mixture by distillation. The other variant is characterized by the presence of an aqueous catalyst phase, separate from the reaction product, which comprises rhodium carbonyl complexes and a sulfonated or carboxylated organic phosphine. This variant permits isolation of the hydroformylation products without use of thermal process steps, simplifies catalyst recovery and produces a particularly high proportion of unbranched aldehydes when terminal olefins are used.

Both of these processes are frequently described in the literature, for example in W. A. Herrmann, C. W. Kohlpaintner, Angew. Chem. 1993,105, p. 1588 and also in DE-C-26 27 354 and EP-B-0 103 810.

In the processes which have been implemented in industry, the rhodium catalyst is used in the form of hydridorhodium carbonyls which contain additional ligands, in particular tertiary organic phosphines or phosphites. In most cases, the ligands are present in excess relative to the metal atom, so that the catalyst system consists of complex compounds and a free ligand. Use of the rhodium catalysts described makes it possible to carry out the hydroformylation reaction at pressures below 300 bar.

The different way in which the reaction is carried out affects inter alia the extent of conversion of starting materials and the formation of by-products. In general, the process in the two-phase reaction medium gives better conversions at higher selectivity than the homogeneous (single-phase) process. An advantage of the reaction in the system with separate catalyst phase is the trouble-free removal of the catalyst. It can be removed by simple separation of aqueous and organic phases, i.e. without distillation and thus without thermal process steps. On the other hand, in single-phase homogeneous catalyzed processes, the reaction product has to be distilled off from the catalyst, or the catalyst has to be separated off from the crude product by another method. Due to the thermal sensitivity of the reaction products, distillation is frequently associated with losses in yield. Other process variants, such as, for example, precipitation or membrane separation of the catalyst are industrially complex and thus disadvantageous.

The two-phase hydroformylation process has proven successful for the hydroformylation of propene and 1-butene (from butene mixtures, e.g. raffinate 2) on an industrial production scale. It is known as the Ruhrchemie/Rhône-Poulenc process. The catalyst system used is a hydridorhodium carbonyl complex which is modified and stabilized by the water-soluble ligands TPPTS (triphenylphosphine trisulfonate sodium salt).

The TPPTS ligand, which is water-soluble by virtue of the sulfonato groups, has the function of solubilizing the rhodium complex in the water phase and of preventing loss of the rhodium complex into the organic phase. The chemical reaction, i.e. the complex-catalyzed addition of a hydrogen and a carbon monoxide molecule to the double bond takes place, according to current understanding, either in the aqueous catalyst phase or in the phase interface. The product formed can pass into the organic phase by adjusting the phase equilibrium.

For the hydroformylation of higher olefins, i.e. olefins having more than 6 carbon atoms, the Ruhrchemie/Rhône-Poulenc process is unsuitable since only very low space-time yields are obtained. The decrease in the rate of the reaction during the two-phase hydroformylation of olefins, which is observed with increasing carbon number, is generally attributed to the poorer solubility of the higher olefins in the water phase. Since the two-phase hydroformylation process has both the advantage of relatively mild reaction conditions, as well as permitting simple separation of the product phase from the catalyst phase, there is an industrial interest in also hydroformylating higher olefins by this process.

The hydroformylation products of higher olefins are mostly used as intermediates for the preparation of higher alcohols and, to a lesser extent, for the preparation of medium- to long-chain carboxylic acids by oxidation, or for the synthesis of amines by reductive amination of aldehydes. Moreover, straight-chain aldehydes having seven or more carbon atoms are used in the fragrance industry as such or in the form of their acetals for perfumes or for perfuming soaps. Linear and branched alcohols having from 8 to 12 carbon atoms are used industrially on a large scale as plasticizer alcohols, which are in most cases used in the form of their bisphthalates or bismaleates as plasticizers for plasticized PVC. Other fields of application for higher, largely linear alcohols are components for detergents, coating base materials and enameling base materials (Ullmann's Encyclopedia of Industrial Chemistry, 4th edition, Vol. 7, publisher Chemie Weinheim 1974, p. 118–141). Catalysts for the hydroformylation are also known from J. prakt. Chem. 338 (1996), 124–128.

The object was to develop a process which permits higher molecular weight olefinically unsaturated compounds to be hydroformylated with the highest possible activity and selectivity to give the corresponding aldehydes. Moreover, it should be possible to readily separate reaction product and catalyst system from one another, and noble metal losses should be largely avoided.

This object is achieved by a catalyst comprising rhodium and a compound of the formula (I)

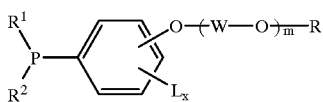
(I)

in which
m is a number from 1 to 1000, preferably from 2 to 300, particularly preferably from 2 to 100;
x is a number from 0 to 4, preferably 0 or 1;
W is a group of the formulae $-CH_2-CH_2-$, $-CH(CH_3)CH_2-$ or $-CH_2CH(CH_3)-$;
R is hydrogen, a straight-chain or branched $C_1-C_5$-alkyl radical; or a group of the formulae

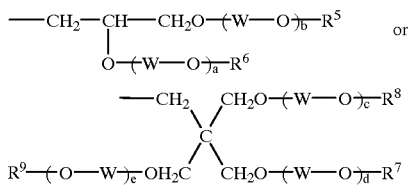

where
a, b, c, d and e independently of one another are a number from 0 to 1000, at least one of the numbers a, b, c, d and e being greater than 0;
$R^5$, $R^6$, $R^7$, $R^8$ and $R^9$ are identical or different and are hydrogen, $C_1-C_5$-alkyl or a group of the formula

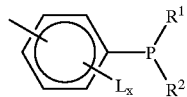

$R^1$ and $R^2$ are identical or different and are a straight-chain, branched or cyclic $C_1-C_{30}$-alkyl radical or $C_6-C_{10}$-aryl radical, which is unsubstituted or substituted by from one to five $C_1-C_3$-alkyl radicals, or $R^1$ and $R^2$ together with the trivalent P atom form a dibenzophospholyl of the formula

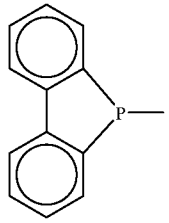

or a 3,4-dimethyiphospholyl of the formula

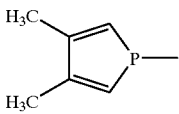

and
L is $C_1-C_5$-alkyl, $C_1-C5$-alkoxy, $NO_2$, $NR^3R^4$, where $R^3$ and $R^4$ independently of one another are hydrogen or $C_1-C_4$-alkyl, or L is Cl or OH.

The alkylene glycol groups on the phenyl ring can be in the ortho, meta or para position relative to the phosphorus atom. The oxalkylene chain on which the group $-(W-O-)_m$ is based can consist exclusively of ethylene oxide units or exclusively of propylene oxide units or of a combination of these units in any order.

Of particular interest are compounds of the formula (I) in which $R^1$ and $R^2$ are identical and are each a straight-chain or branched $C_1-C_6$-alkyl radical, a cyclohexyl radical or a phenyl radical.

Also of particular interest are compounds of the formula (I) in which R is hydrogen, methyl, ethyl, n-propyl, n-butyl or a group of the formula

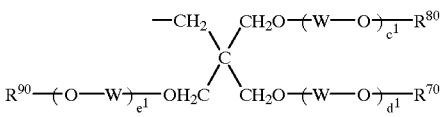

in which $c^1$, $d^1$ and $e^1$ independently of one another are a number from 1 to 500, in particular from 2 to 300, and $R^{70}$, $R^{80}$ and $R^{90}$ are identical or different and are hydrogen, methyl, ethyl, n-propyl or n-butyl.

Also of particular interest are compounds of the formula (I) in which L is methoxy, ethoxy, methyl, ethyl or OH, or in which x is 0.

Examples of compounds of the formula (I) are methyl triphenylphosphin-4-yl triethylene glycol ether, methyl triphenylphosphin-3-yl triethylene glycol ether, methyl triphenylphosphin-2-yl triethylene glycol ether, and compounds having longer oxalkyl chains, the ethoxy and propoxy units being in any order and as a rule forming a product mixture:

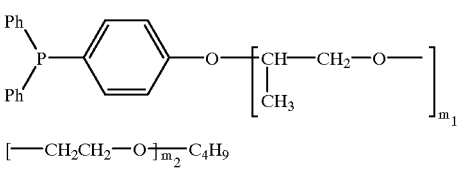

in which $m_1$ and $m_2$ are each 16 and Ph is phenyl;

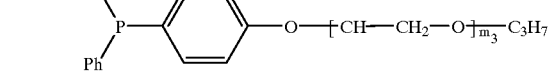

in which $m_3$ is about 22;

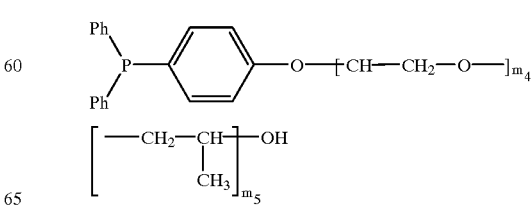

in which $m_4$ is about 84 and $m_5$ is about 21,

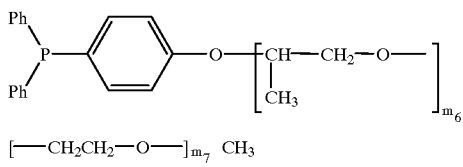

[—CH$_2$CH$_2$—O—]$_{m_7}$ CH$_3$ in which $m_6$ is about 22 and $m_7$ is 5.5.

Compounds of the formula (I) can be prepared by deprotonating a hydroxyphenylphosphine of the formula (II)

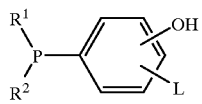 (II)

using a base to give the corresponding phenoxide, and reacting with a compound of the formula (III)

 (III)

in which W, R and m are as defined above, and X is a nucleophilically substitutable leaving group, to give the compound of the formula (I).

Examples of nucleophilically substitutable leaving group X are ortho- meta- or para-toluenesulfonate, methanesulfonate, trifluoro acetate, trifluoromethanesulfonate, nonafluorobutylsulfonate, benzenesulfonate, p-nitrobenzenesulfonate, Cl or Br.

Suitable bases are, for example, NaOH, KOH, NaH, KH or trialkylamine. Preference is given to triethylamine and KOH.

The reaction is expediently carried out at temperatures between 20 and 100° C., preferably between 60 and 90° C. Since the deprotonation stage is generally exothermic, at this point in the synthesis, cooling may be expedient, for example to from 0 to 20° C. The process can be carried out in the presence or absence of organic solvents. Suitable organic solvents are, in particular, dimethyl formamide, toluene or ethyl acetate. It is further advantageous to carry out the reaction under an inert-gas atmosphere.

The catalyst can be prepared in a simple manner by bringing together rhodium, for example in the form of a salt or a complex, and the compound of the formula (I). Examples of such salts or complexes are rhodium acetate, rhodium butyrate, rhodium chloride, rhodium acetylacetonate, rhodium nitrate, [RhCl(CO)$_2$], [Rh(acac)(CO)$_2$] and HRh(CO)(TPP)$_3$, where acac is acetylacetonate and TPP is triphenylphosphine. It is particularly favorable to dissolve the rhodium in the form of a water-soluble salt or complex together with a compound of the formula (I) in water. It is also possible to firstly dissolve the rhodium salt or the rhodium complex and then add the compound of the formula (I) or, in reverse, firstly dissolve the compound of the formula (I) and then add the rhodium salt or the rhodium complex.

It is possible to use the catalyst comprising rhodium and the compound of the formula (I) directly in the hydroformylation, i.e. without additional treatment.

It is, however, also possible to firstly subject the catalyst comprising rhodium and the compound of the formula (I) to a pretreatment in the presence of hydrogen and carbon monoxide under pressure and, if necessary, at elevated temperature and, by means of this preconditioning, to prepare the actually active catalyst species. The conditions for the preconditioning can correspond to the conditions of a hydroformylation.

The catalyst usually comprises rhodium and the compound of the formula (I) in a molar ratio of from 1:1 to 1:5000, in particular from 1:100 to 1:3000. In a number of cases, a catalyst comprising rhodium and the compound of the formula (I) in a molar ratio of from 1:1 to 1:1500, in particular from 1:1 to 1:200, preferably from 1:50 to 1:150 has also proven suitable. In general, increasing amounts of phosphine ligands effect a reduction in the loss of noble metal into the organic phase during the hydroformylation.

The present invention further provides a process for the preparation of aldehydes. It comprises reacting an olefinic compound having from 3 to 20 carbon atoms with carbon monoxide and hydrogen in the presence of a catalyst comprising rhodium and a compound of the general formula (I) at a pressure of from 10 to 500 bar and a temperature of from 40 to 200° C. in a reaction mixture which comprises an aqueous and an organic phase.

The liquid organic phase essentially consists of the substrate olefin and/or the reaction product of the hydroformylation and, where necessary, one or more organic solvents. If a solvent is used, it may be chosen from inert aliphatic compounds, such as alkanes, preferably $C_5$–$C_9$-alkanes, such as cyclohexane and n-pentane, or aromatic compounds, such as toluene, xylene, ethylbenzene, mesitylene or chlorobenzene.

The aqueous phase comprises the catalyst and the compound of the formula (I). It is advantageous to form the catalyst in situ from the abovedescribed rhodium salt or rhodium complex and the compound of the formula (I) in the aqueous phase during the hydroformylation according to the invention. As mentioned above, it is advantageous if the catalyst comprises a stoichiometric excess of the phosphine of the formula (I).

A stoichiometric excess of the phosphine is thus advantageously added to the reaction mixture in order to form the catalytic complex and to provide free phosphine. The free phosphines can be identical or different to those used for the formation of the catalytic complex, although it is preferable to use the same ones.

The volume ratio of organic phase to aqueous catalyst phase should be between 5:1 and 1:5. Preference is given to a range from 3:1 to 1:2. Low quotients of aqueous to organic phase in most cases effect a slowing of the reaction rate. In the case of high volume ratios of aqueous to organic phase, the loss of rhodium into the organic phase is higher.

The olefinic compound may comprise one or more as a carbon-carbon double bond. The carbon-carbon double bond can be positioned at the end or internally. Preference is given to olefinic compounds with a terminal carbon-carbon double bond.

Examples of α-olefinic compounds (having a terminal carbon-carbon double bond) are alkenes, alkyl alkenoates, alkylene alkanoates, alkenyl alkyl ethers and alkenols, in particular those having from 6 to 14 carbon atoms. Without laying claim to completeness, α-olefinic compounds which may be mentioned are propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,7-octadiene, 3-cyclohexyl-1-butene, hex-1-en-4-ol, oct-1-en-4-ol, vinylcyclohexene, n-propyl-7-octenoate, 7-octenoic acid and 5-hexenamide.

Examples of other suitable olefinic compounds which may be mentioned are 2-butene, diisobutylene, tripropylene, ®Octol or ®Dimersol (dimerization products of butenes), tetrapropylene, cyclohexene, cyclopentene, dicyclopentadiene, acyclic, cyclic or bicyclic terpenes, such as myrcene, limonene and pinene.

The abovedescribed catalyst comprising rhodium and the compound of the formula (I) is usually used in an amount of from 5 to 100 mg, preferably from 30 to 60 mg, of rhodium per kilogram of aqueous phase.

The amount of rhodium relative to the olefinic compound is expediently from 1:500 to 1:100,000, preferably from 1:10,000 to 1:80,000, mol of rhodium per mole of olefinic compound. The fact that such small amounts of rhodium suffice for a two-phase process is extremely surprising.

In the process according to the invention rhodium loss into the organic phase is in most cases below 1 ppm.

The pH of the aqueous phase should preferably be at pH 5 to 8. If a buffer is used, it should be compatible with the catalyst and be inert.

The reaction is carried out in the presence of hydrogen and carbon monoxide (synthesis gas). The molar ratio of hydrogen to carbon monoxide can be chosen within wide limits and is usually from 1:10 to 10:1, in particular from 5:1 to 1:5, preferably from 2:1 to 1:2. The process is particularly simple if hydrogen and carbon monoxide are used in a molar ratio of 1:1 or approximately 1:1.

In a large number of cases, it has proven advantageous to carry out the reaction at a pressure of from 20 to 400 bar, in particular from 30 to 80 bar. While 80 bar is preferable from the point of view of activity, a synthesis gas pressure of 30 bar gives better selectivities with respect to the n/iso ratio.

The reaction of the olefinic compounds with hydrogen and carbon monoxide takes place at temperatures of from 40 to 200° C. Below 40° C. the reaction rate is unacceptably slow, whereas catalyst deactivation can take place at temperatures above 200° C. A preferred range is from 80 to 150° C., particularly preferably from 110 to 130° C., since these temperatures give the best results with respect to selectivity to aldehydes, combined with an acceptable reaction rate.

At this point, it should be pointed out that the reaction conditions, in particular rhodium concentration, pressure and temperature also depend on the nature of the olefinic compound to be hydroformylated. Relatively reactive olefinic compounds require low rhodium concentrations, low pressures and low temperatures. In contrast, the reaction of relatively unreactive olefinic compounds requires greater rhodium concentrations, higher pressures and higher temperatures.

The process can be carried out particularly successfully if an α-olefinic compound is used. It is, however, also possible to react other olefinic compounds having internal carbon-carbon double bonds.

After a discontinuous reaction is complete, the hydroformylation mixture is freed from carbon monoxide and hydrogen by depressurization, and the organic product phase is separated from the aqueous catalyst phase by phase separation. The process according to the invention can, however, also be carried out continuously.

EXPERIMENTAL SECTION

Preparation of a Compound of the Formula (I)

The preparation of compounds of the formula (I) is described in the German Patent Application (file reference 196 30534.9) filed on the same date as the present patent application.

Preparation of the Catalyst 1) 0.7 mg of rhodium(III) acetate and 36 g of the ligand P-(P41/300)-triphenylphosphine prepared in accordance with Example 4 of the abovementioned German Patent Application (file reference P 196 30534.9) are dissolved in 30 ml of water corresponding to a Rh:ligand molar ratio of 1:2500, and maintained at 125° C. for 3 h in a 200 ml steel autoclave at a synthesis pressure of 25 bar ($CO/H_2$=1:1).

EXAMPLE 1

Hydroformylation of 1-hexene 30 ml of 1-hexene were metered into the abovementioned steel autoclave containing the catalyst using a pump under the existing pressure of 25 bar, and the mixture is stirred for 3 hours at 125° C. The synthesis gas pressure was increased to 80 bar and kept constant within a pressure band of 5 bar. At the end of the reaction, the stirrer and heating were switched off, and after a settling period of from 30 to 60 min, the upper product phase was separated from the catalyst phase by phase separation. The degree of conversion of the product phase was analyzed using gas chromatography (GC) and $^1$H-NMR spectroscopy:

Conversion (according to GC) in an experimental series of 5 cycles running one after the other with the same catalyst phase: 97.9%; 98.4%, 98.1%, 97.2%, 90.4%. Ratio of n-heptanal:isoheptanal (according to GC): 71:29.

EXAMPLES 2 TO 5

The procedure was as given in Example 1, but the olefinic compound (in each case 120 mmol) and the synthesis gas pressure were changed as given in the table below:

| Olefin | Amount of olefin in ml | Synthesis gas pressure in bar | Conversion in % (GC) | Ratio of n:iso (GC) |
| --- | --- | --- | --- | --- |
| 1-Octene | 18.9 | 30 | 83.4 | 77:23 |
| 1-Dodecene | 26.8 | 30 | 35.1 | 77:23 |
| 1-Hexene | 15.9 | 80 | 92.8 | 72:28 |
| 1-Octene | 18.9 | 80 | 97.5 | 73:27 |

EXAMPLE 6

Experimental Series with 1-octene (7 cycles)

The procedure was as given in Example 1, but using 37.7 ml of 1-octene as olefin. The following conversions and n:isononanal ratios were obtained in the individual reaction cycles:

| Cycle | Conversion in % (GC) | Ratio of n:iso (GC) |
| --- | --- | --- |
| 1 | 97.1 | 71:29 |
| 2 | 97.4 | 71:29 |
| 3 | 97.5 | 71:29 |
| 4 | 97.5 | 70:30 |
| 5 | 97.2 | 71:29 |
| 6 | 95.4 | 70:30 |
| 7 | 97.0 | 69:31 |

EXAMPLE 7

Experimental Series with 1-dodecene (5 cycles)

The procedure was as given in Example 1, but using 53.3 ml of 1-dodecene as olefin. The following conversions and n:iso ratios were obtained in the individual reaction cycles:

| Cycle | Conversion in % (GC) | Ratio of n:iso (GC) |
|---|---|---|
| 1 | 79.3 | 72:28 |
| 2 | 82.0 | 72:28 |
| 3 | 83.4 | 72:28 |
| 4 | 82.2 | 71:29 |
| 5 | 78.1 | 70:30 |

Preparation of the Catalysts used in Examples 8 to 21

General Preparation Procedure:

6 mg of rhodium(III) acetate and the amount, specified in Table I under "initial weight of ligand [g]", of the ligands prepared in accordance with the abovementioned German Patent Application (file reference 19 630 534.9) are dissolved in 30 ml of water corresponding to an Rh:ligand molar ratio of 1:100, and maintained at 125° C. for 3 hours in a 200 ml steel autoclave at a synthesis gas pressure ($CO/H_2$) of 25 bar with stirring (preconditioning). This catalyst solution is used in Examples 8 to 21.

As regards the compounds of the formula (I) used (4'-(diphenylphosphinyl)-phenoxy-polyalkylene glycols), reference may be made to the following summary.

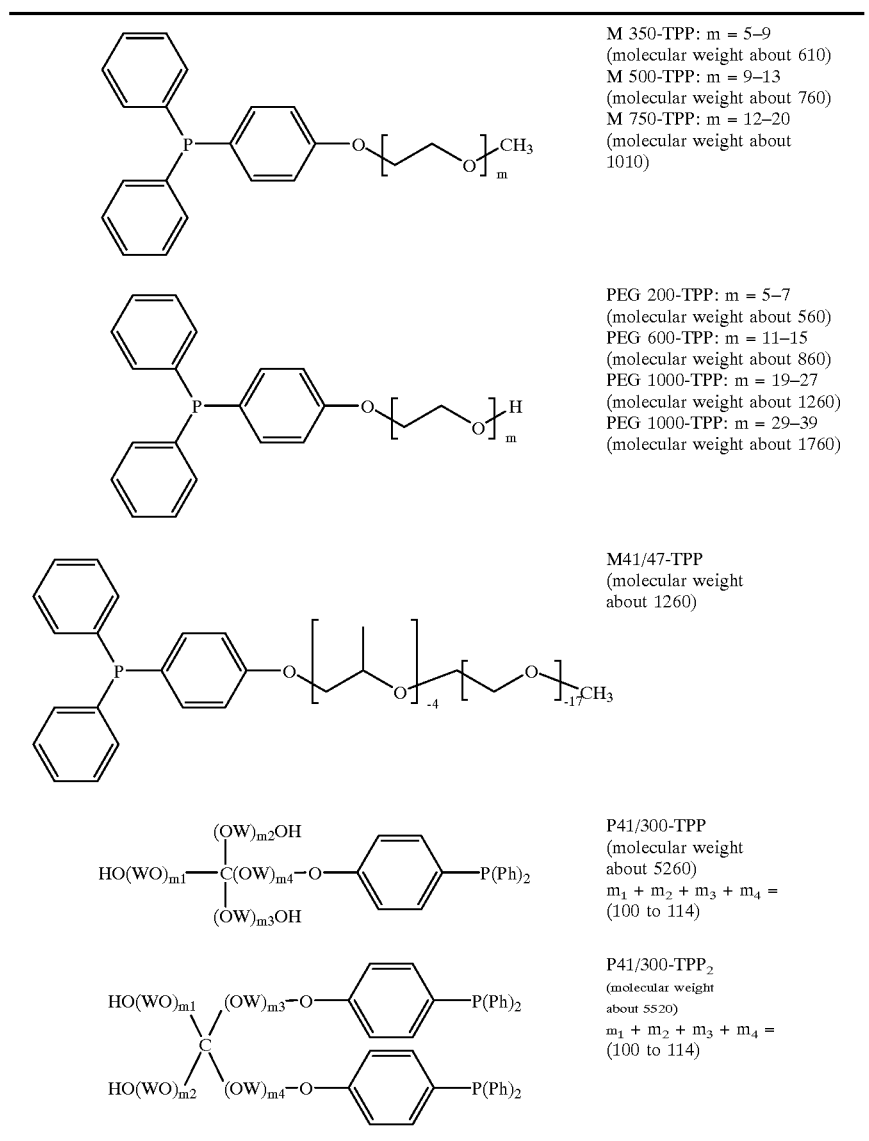

EXAMPLE 8

Hydroformylation of 1-dodecene Using Rh/M41/40-TPP as Catalyst 26.6 ml of 1-dodecene (120 mmol) are metered into the abovementioned steel autoclave containing the catalyst solution using a pump under the existing pressure of 25 bar. The synthesis gas pressure is then increased to 50 bar and kept constant within a pressure band of 5 bar. The reaction temperature is 125° C. After a reaction time of 90 min, no more gas is absorbed and the reaction is stopped by switching off the stirrer. The autoclave is cooled to 25° C. and, after a settling time of 60 min, the upper product phase is separated from the catalyst phase by phase separation. The degree of conversion of the product phase is analyzed by gas chromatography (GC) and $^1$H-NMR spectroscopy.

The conversion according to GC is 93.4%. The n-tridecanol: 2-methyldodecanal ratio is 72:28.

EXAMPLES 9 TO 21

Hydroformylation of 1-dodecene with Various Catalysts Comprising Rhodium and Compounds of the Formula (I)

The examples below are carried out as in Example 8 and with slight changes to the experimental parameters and also using various compounds of the formula (I). The catalyst is prepared in an analogous manner, the initial weights of ligand given in Table I being used. The other experimental parameters and the experimental results obtained are given in Table I.

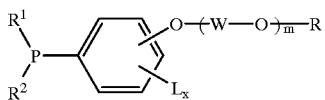

(I)

in which m is a number from 1 to 1000;

x is a number from 0 to 4;

W is a group of the formulae —$CH_2$—$CH_2$—, —CH($CH_3$)$CH_2$— or —$CH_2CH(CH_3)$—;

R is hydrogen, a straight-chain or branched $C_1$–$C_5$-alkyl radical; or a group of the formulae

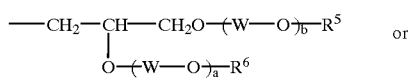

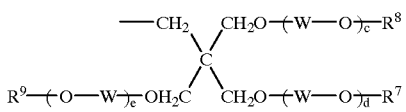

where a, b, c, d and e independently of one another are a number from 0 to 1000, at least one of the numbers a, b, c, d and e being greater than 0;

TABLE I

Hydroformylation of 1-dodecene using catalysts comprising rhodium and compounds of the formula (I)

| Ex. No. | Ligand short form | Initial weight of ligand (g) | Cat. phase solvent [ml] | p [bar] | t [min] | Yield of aldehyde [%] GC | n:iso ratio (GC) | Rh loss org. phase [ppm] |
|---|---|---|---|---|---|---|---|---|
| 8 | M41/40-TPP | 2.91 | 30 ml H$_2$O | 50 | 90 | 93.4 | 72:28 | 0.22 |
| 9 | M41/40-TPP | 2.91 | 30 ml PEG 400 | 50 | 15 | 95.8 | 61:39 | 0.06 |
| 10 | M41/40-TPP | 2.91 | 30 ml H$_2$O | 15 | 60 | 88.0 | 77:23 | 0.25 |
| 11 | M350-TPP | 1.17 | 30 ml H$_2$O | 50 | 15 | 89.1 | 72:28 | 1.9 |
| 12 | M350-TPP | 1.17 | 30 ml H$_2$O | 15 | 30 | 82.4 | 76:24 | 0.65 |
| 13 | M500-TPP | 1.75 | 30 ml H$_2$O | 50 | 30 | 93.0 | 76:24 | 0.34 |
| 14 | M500-TPP | 1.75 | 30 ml H$_2$O | 15 | 60 | 85.4 | 75:25 | 0.21 |
| 15 | M750-TPP | 2.32 | 30 ml H$_2$O | 50 | 45 | 95.0 | 75:25 | 0.34 |
| 16 | M750-TPP | 2.32 | 30 ml H$_2$O | 15 | 180 | 10.1 | 79:21 | <0.05 |
| 17 | PEG200-TPP | 1.06 | 30 ml H$_2$O | 50 | 15 | 90.0 | 73:27 | n.d.* |
| 18 | PEG600-TPP | 1.99 | 30 ml H$_2$O | 50 | 145 | 89.7 | 76:24 | n.d.* |
| 19 | PEG1000-TPP | 2.91 | 30 ml H$_2$O | 50 | 180 | 50.4 | 84:16 | n.d.* |
| 20 | PEG1500-TPP | 4.06 | 30 ml H$_2$O | 50 | 180 | 46.3 | 84:16 | n.d.* |
| 21 | PEG 41/300-TPP | 12.1 | 30 ml H$_2$O | 50 | 180 | 92.5 | 75:25 | n.d.* |

Constant conditions:
Catalyst preparation from 6 mg of rhodium(III) acetate (0.023 mmol), quantity and type of ligands of the formula (I) and solvents as given, Rh:ligand of the formula (I) ratio 1:100, Rh:olefin ratio 1:5280, preconditioning conditions: 3 hours at a synthesis gas pressure of 25 bar
Hydroformylation conditions: T = 125° C., reaction pressure as given, reaction time as given (until no more gas is absorbed); phase separation at room temperature,
*n.d. = not determined

What is claimed is:

1. A catalyst comprising rhodium and a compound of the formula (I)

$R^5$, $R^6$, $R^7$, $R^8$ and $R^9$ are identical or different and are hydrogen, $C_1$–$C_5$-alkyl or a group of the formula

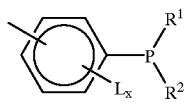

$R^1$ and $R^2$ are identical or different and are a straight-chain, branched or cyclic $C_1$–$C_{30}$-alkyl radical or $C_6$–$C_{10}$-aryl radical, which is unsubstituted or substituted by from one to five $C_1$–$C_3$-alkyl radicals, or $R^1$ and $R^2$ together with the trivalent P atom form a dibenzophospholyl of the formula

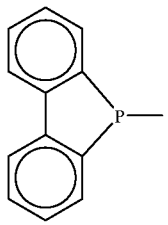

or a 3,4-dimethylphospholyl of the formula

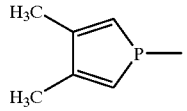

and

L is $C_1$–$C_5$-alkyl, $C_1$–$C_5$-alkoxy, $NO_2$, $NR^3R^4$, where $R^3$ and $R^4$ independently of one another are hydrogen or $C_1$–$C_4$-alkyl, or L is Cl or OH.

2. The catalyst as claimed in claim 1, wherein $R^1$ and $R^2$ are identical and are each a straight-chain or branched $C_1$–$C_6$-alkyl radical, a cyclohexyl radical or a phenyl radical.

3. The catalyst as claimed in claim 1, wherein R is hydrogen, methyl, ethyl, n-propyl, n-butyl or a group of the formula

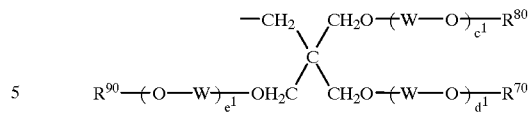

in which $c^1$, $d^1$ and $e^1$ independently of one another are a number from 1 to 500, and $R^{70}$, $R^{80}$ and $R^{90}$ are identical or different and are hydrogen, methyl, ethyl, n-propyl or n-butyl.

4. The catalyst as claimed in claim 1, wherein L is methoxy, ethoxy, methyl, ethyl or OH.

5. The catalyst as claimed in claim 1, wherein x is 0.

6. The catalyst as claimed in claim 1, which comprises rhodium and the compound of the formula (I) in the molar ratio from 1:1 to 1:200.

7. The catalyst as claimed in claim 1 where $c^1$, $d^1$, and $e^1$ independently a number from 2 to 300.

8. A process for the preparation of a catalyst as claimed in claim 1, which comprises bringing together a rhodium salt or a rhodium complex and a compound of the formula (I).

9. The process as claimed in claim 8, wherein the rhodium salt or the rhodium complex and the compound of the formula (I) are dissolved in water.

10. A process for the preparation of aldehydes, comprising reacting an olefinic compound having from 3 to 20 carbon atoms with carbon monoxide and hydrogen in the presence of a catalyst of the formula (I) as claimed in claim 1 at a pressure from 10 to 500 bar and a temperature of from 40 to 200° C. in a reaction medium which comprises an aqueous and an organic phase.

11. The process according to claim 10, wherein the olefinic compound is an α-olefinic compound.

12. The process as claimed in claim 10, wherein the catalyst is present in an amount corresponding to from $10^{-5}$ to $2 \times 10^{-3}$ mol of rhodium per mole of olefinic compound.

13. The process as claimed in claim 10, wherein the reaction with carbon monoxide and hydrogen is carried out at a pressure of from 30 to 80 bar.

14. The process as claimed in claim 9, wherein the reaction is carried out at a temperature of from 80 to 150° C.

* * * * *